(12) United States Patent
Tan et al.

(10) Patent No.: US 6,759,038 B2
(45) Date of Patent: *Jul. 6, 2004

(54) METASTASIS MODELS USING GREEN FLUORESCENT PROTEIN (GFP) AS A MARKER

(75) Inventors: Yuying Tan, San Diego, CA (US); Takashi Chishima, Yokohama (JP)

(73) Assignee: AntiCancer, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,268

(22) Filed: May 29, 2001

(65) Prior Publication Data

US 2002/0026649 A1 Feb. 28, 2002

Related U.S. Application Data

(63) Continuation of application No. 09/226,856, filed on Jan. 7, 1999, now Pat. No. 6,251,384, which is a continuation-in-part of application No. 09/067,734, filed on Apr. 28, 1998, now Pat. No. 6,235,968, which is a continuation-in-part of application No. 09/049,544, filed on Mar. 27, 1998, now Pat. No. 5,235,967, which is a continuation-in-part of application No. 08/848,539, filed on Apr. 28, 1997, now Pat. No. 6,232,523.

(51) Int. Cl.[7] .................... A61K 48/00; C12N 5/00; C12N 15/63
(52) U.S. Cl. ............... 424/93.21; 800/8; 800/9; 800/10; 435/320.1; 435/325; 435/455; 514/44
(58) Field of Search ................. 435/325, 320.1, 435/455; 800/8, 9, 10; 514/44; 424/93.2, 93.21

(56) References Cited

U.S. PATENT DOCUMENTS

| 5,650,135 | A | 7/1997 | Contag et al. ............. 424/9.1 |
| 5,874,304 | A | 2/1999 | Zolotukhin et al. ......... 435/366 |

FOREIGN PATENT DOCUMENTS

| WO | WO 97/18841 | 5/1997 |
| WO | WO 97/45550 | 12/1997 |
| WO | WO 98/49336 | 11/1998 |

OTHER PUBLICATIONS

Merriam–Webster Online, http://www.m-w.com/cgi-bin/dictionary, definition of "intact". 2003.*
Fu, X. et al., *Anticancer Res.* (1993) 13:283–286.
Heim, R. et al., *Nature* (1995) 373:663–664.
Hoffman, R.M., *Cancer Cells* (1991) 3:86–92.
Hoffman, *Investigational New Drugs* (1999) 17(4):343–359.
Hyer, M. L. et al., *Cancer Gene Therapy* (1997) 4(6):s29–s30.
Kaufman, R.J. et al., *Nucleic Acids Res.* (1991) 19:4485–4490.
Kaufman et al., *Annu. Rev. Immunol.* (1995) 13:339–367.
Khokha, R. et al., *Cancer Metastasis Rev.* (1995) 14:279–301.
Koop, S. et al., *Cancer Res.* (1995) 55:2520–2523.
Leighton, J., *Cancer Res.* (1957) 17:929–941.
Leighton, J., *Cancer Res.* (1960) 20:575–597.
Levy, J.P. et al., *Nature Biotechnol.* (1996) 14:610–614.
Li, Y. et al., *Biotechnologies*, (1997) 23:1026–1029.
Lin, W.C. et al., *Cancer Res.* (1990) 50:2808–2817.
Lin, W.C. et al., *Invasion and Metastasis* (1992) 12:197–209.
Margolis, L.B. et al., *In Vitro Cell Dev. Biol.* (1995) 31:221–226.
Margolis et al., *Annu. Rev. Immunol.* (1995) 13:339–367.
Miller et al., *FASEB* (1995) 9:190–199.
Morin, J. et al., *J. Cell. Physiol.* (1972) 77:313–318.
Plautz, J. D. et al., *Gene* (1996) 173:83–87.
Prasher, D.C. et al., *Gene* (1992) 111:229–233.
Romer et al., *APMIS* (1995) 103:582–587.
Vieweg et al., *Cancer Invest.* (1995) 13(2):193–201.
Yang et al., *Cancer Research* (1999) 59(4):781–786.
Yang et al., *Proc. SPIE–Int. Soc. Opt. Eng.* (1999) 117–124.
Yokoe, H. et al., *Nature Biotechnol.* (1996) 14:1252–1256.
Zolotukhin, S. et al., *J. Virol.* (1996) 70:4646–4654.
Aboody–Guterman et al., *Society for Neuroscience Abstracts* (1996) 22:949–1998.
Astoul, P. et al., *Anticancer Res.* (1994) 14:85–92.
Astoul, P. et al., *J. Cell Biochem.* (1994) 56:9–15.
Chalfie, M. et al., *Science* (1994) 263:802–805.
Chishima et al., *Proc. Am. Assoc. Canc. Res* (1997) 38:489 (#3276–3/97).
Chishima, T. et al., *Clinical and Experimental Metastais* (1997) 15(5):547–552.
Chishima, T. et al., *AnticancerRes.* (1997) 17:2377–2384.
Chishima, T. et al., *Cancer Res.* (1997) 57(10):2042–2047.
Chishima, T. et al., *Proc. Nat'l Academy of Sciences of USA* (1997) 94:11573–11576.
Cody, C.W. et al., *Biochemistry* (1993) 32:1212–1218.
Cormack, B. et al., *Gene* (1996) 173:33–38.
Crameri, A. et al., *Nature Biotechnol.* (1996) 14:315–319.
Delagrave, S. et al., *Biotechnology* (1995) 13:151–154.

* cited by examiner

Primary Examiner—Anne M. Wehbe'
(74) Attorney, Agent, or Firm—Morrison & Foerster LLP

(57) ABSTRACT

A method to follow the progression of metastasis of a primary tumor, which method comprises removing fresh organ tissues from a vertebrate subject which has been modified to contain tumor cells that express GFP and observing the excised tissues for the presence of fluorescence is disclosed. The fluorescence can also be monitored by observing the tissues in situ. Vertebrate subjects which contain GFP producing tumors are useful models to study the mechanism of metastasis, as well as to evaluate candidate protocols and drugs. In addition, subjects already harboring tumors can be treated so as to modify the endogenous tumors to contain GFP. This permits clinical applications. Finally, by injecting a contrast dye into a subject harboring a GFP-labeled tumor, angiogenesis in the tumor can be observed directly.

12 Claims, 2 Drawing Sheets

METASTASIS MODELS USING GREEN FLUORESCENT PROTEIN (GFP) AS A MARKER

This application is a Continuation of U.S. Ser. No. 09/226,856, filed Jan. 7, 1999, now U.S. Pat. No. 6,251,384, which is a Continuation-in-part of U.S. Ser. No. 09/067,734, filed Apr. 28, 1998, now U.S. Pat. No. 6,235,968, which is a Continuation-in-part of U.S. Ser. No. 09/049,544, filed March 27, 1998, now U.S. Pat. No. 5,235,967, which is a Continuation-in-part of U.S. Ser. No. 08/848,539, filed April 28, 1997, now U.S. Pat. No. 6,232,523, the contents of which are incorporated by reference.

TECHNICAL FIELD

The invention relates to the study of tumor progression. Specifically, it concerns model systems for studying the metastasis of tumors in vertebrate systems and to models and methods for evaluating candidate drugs.

BACKGROUND ART

It has long been recognized that the ability of tumor tissues to metastasize constitutes a major portion of the life-threatening aspects of malignancy. Metastasis is the growth of secondary tumors at sites different from the primary tumor. Thus, despite surgical removal of the primary tumor, it may not be possible to arrest the progress of this condition. An understanding of the mechanism whereby metastasis occurs will be crucial to the development of protocols whereby the growth of secondary tumors can be controlled. In order to understand the mechanism of metastasis, it will be necessary to provide a model which permits identification of small numbers of tumor cells against a background of many host cells so that secondary tumor emboli and micrometastases can be observed over the course of real time.

Others have demonstrated extravasation and initial seeding steps in tumor metastasis in vitro using externally fluorescently labeled tumor cells. Khokha, R. et al., *Cancer Metastasis Rev* (1995) 14:279–301; Koop, S. et al., *Cancer Res* (1995) 55:2520–2523. Further, Margolis, L. B. et al., *In Vitro Cell Dev Biol* (1995) 31:221–226 was able to visualize the migration of externally fluorescently labeled lung tumor cells in host mouse lung in histoculture. In all cases, however, long-term observation was not possible due to the limitation of exogenous fluorescent labels. Retroviral transfer of a green fluorescent protein (GFP) gene has been shown to result in stable transfectants of human cancer cells in vitro (Levy, J. P. et al., *Nature Biotechnol* (1996) 14:610–614), as well as of hematopoietic cells (Grignani, F. et al. *Cancer Res* (1998) 58:14–19 and by Cheng, L. et al. *Gene Therapy* (1997) 4:1013–1022).

Attempts have been made to provide such a model using the β-galactosidase gene as a marker (Lin, W. C. et al., *Cancer Res* (1990) 50:2808–2817; Lin, W. C. et al., *Invasion and Metastasis* (1992) 12:197–209). However, this marker has not proved satisfactory, as fresh or processed tissue cannot be used. The present invention provides a marker which permits visualization of tumor invasion and micrometastasis formation in viable fresh tissue. In addition, by providing suitable contrast media, the method of the invention can be adapted to visualize angiogenesis in established and growing tumors. The methods of the invention can be applied not only to models of tumor growth and metastasis, but, through the use of retroviral vectors, can be employed to obtain clinical data in human subjects bearing tumors.

The present invention utilizes green fluorescent protein (GFP) as a marker. Heterologous expression of this protein, principally to monitor expression of fused DNA, was disclosed in U.S. Pat. No. 5,491,084. This document describes the expression of GFP in *E. coli* and *C. elegans* and postulates that cells in general can be modified to express GFP. Such expression, according to this document, permits not only a method to monitor expression of fused DNA, but also a means of monitoring protein localization within the cell.

The aspect of the invention which provides a metastatic model has been reported and described in a series of publications. Chishima, T. et al. *Cancer Research* (1997) 57:2042–2047 describe the construction of a dicistronic vector containing the gene for humanized green fluorescent protein (GFP) and dihydrofolate reductase (DHFR). This vector was transfected into CHO-K1 cells to obtain clone-38. Clone-38 showed stable GFP expression which was maintained in the presence of methotrexate (MTX). Clone-38 cells were injected into mice to obtain tumor fragments which were then implanted by surgical orthotopic implantation (SOI) on the ovarian serosa in nude mice. Metastasis could be followed in this model.

Chishima, T. et al. *Proc Natl Acad Sci USA* (1997) 94:11573–11576 describe the preparation of clone-26 by transfection of Anip 973 human lung adenocarcinoma cells with the codon optimized hGFP-S65T clone obtained from Clontech. Clone-26 was injected intravenously into nude mice and the resulting tumors were followed in histoculture.

Chishima, T. et al. *Clin Exp Metastasis* (1997) 15:547–552 and Chishima, T. et al. *Anticancer Res* (1997) 17:2377–2384 describe similar work with clone-26 wherein the cells were inoculated subcutaneously into nude mice resulting in a visualizable tumor which was then implanted into the visceral pleura of nude mice by SOI. Metastases were observed in this model as well.

Chishima, T. et al. *In Vitro Cell Dev Biol* (1997) 33:745–747 describe histoculture of clone-26 and visualization of growth using the fluorescence emitted by GFP.

Yang, M., et al., *Cancer Res* (1998) 58:4217–4221 describe transduction of the human lung cancer cell line H460 with a retroviral expression vector containing enhanced GFP to obtain a stable high-GFP-expressing clone. Cells from this cell line were injected into nude mice and the resulting subcutaneously growing labeled tumors were transplanted by SOI into the left lung of nude mice. Fluorescence could then be observed from the metastases in the collateral lung, pleural membrane and throughout the skeletal system.

Yang, M., et al., *Cancer Res* (In Press) report similar studies using a model for prostate tumor and showing fluorescence throughout the skeletal system in nude mice.

The contents of the foregoing publications are incorporated herein by reference.

In addition to the foregoing, Cheng, L., et al., *Gene Therapy* (1997) 4:1013–1022, describe the modification of hematopoietic stem cells using the GFP gene under control of a retroviral promoter. Although the authors state that human stem cells are transfected with this system only with difficulty, by using an enhanced form of the GFP, satisfactory brightness could be achieved.

In addition, Grignani, F., et al., *Cancer Res* (1998) 58:14–19, report the use of a hybrid EBV/retroviral vector expressing GFP to effect high-efficiency gene transfer into human hematopoietic progenitor cells.

Vectors containing various modified forms of GFP to provide various colors are marketed by Clontech. The Clontech vectors intended for mammalian cell expression place the GFP under control of the cytomegalovirus (CMV) promoter.

DISCLOSURE OF THE INVENTION

The invention provides models which permit the intimate study of formation of metastases from primary tumors in a realistic and real-time setting. By using green fluorescent protein (GFP) as a stable and readily visualized marker, the progression of such metastasis can be modeled and the mechanism elucidated.

Thus, in one aspect, the invention is directed to a method to follow the progression of metastasis of a primary tumor, which method comprises removing fresh organ tissues from a vertebrate subject which has been modified to contain tumor cells that express GFP and observing the excised tissues for the presence of fluorescence.

In one embodiment, however, it is unnecessary to remove organ tissues; rather, the fluorescence can be visualized in the whole animal by real-time fluorescence optical tumor imaging (FOTI).

In another aspect, the invention is directed to a vertebrate subject which has been modified to contain tumor cells expressing GFP.

In these aspects, the vertebrate subject may constitute a model system, such as an immunocompromised mouse wherein tumor cells or a tumor, modified to express green fluorescent protein has been introduced into the subject. The model system may be used to evaluate candidate drugs for their capacity to inhibit metastasis. Alternatively, the subject may be a human or other vertebrate which natively contains the tumor, but wherein the tumor has been subjected to viral infection or to transfection with a retroviral vector so as to produce said GFP. The efficacy of drugs administered to such patients can be evaluated by following the course of metastasis in the subject.

In still other aspects, the invention is directed to tumor cells modified to produce GFP under control of heterologous control elements, to cells that are immortalized to provide stable cell lines as well as comprising visible amounts of GFP, to tissues containing metastatic tumors that produce GFP, and to histocultures of tissues which contain such metastasized tumors.

The invention also includes a method to observe and follow angiogenesis in solid tumors which method comprises (usually) exposing and observing said tumors. The tumors will have been modified to express GFP, and the subject will have been administered a contrast dye to permit this observation.

MODES OF CARRYING OUT THE INVENTION

Figure 1A:
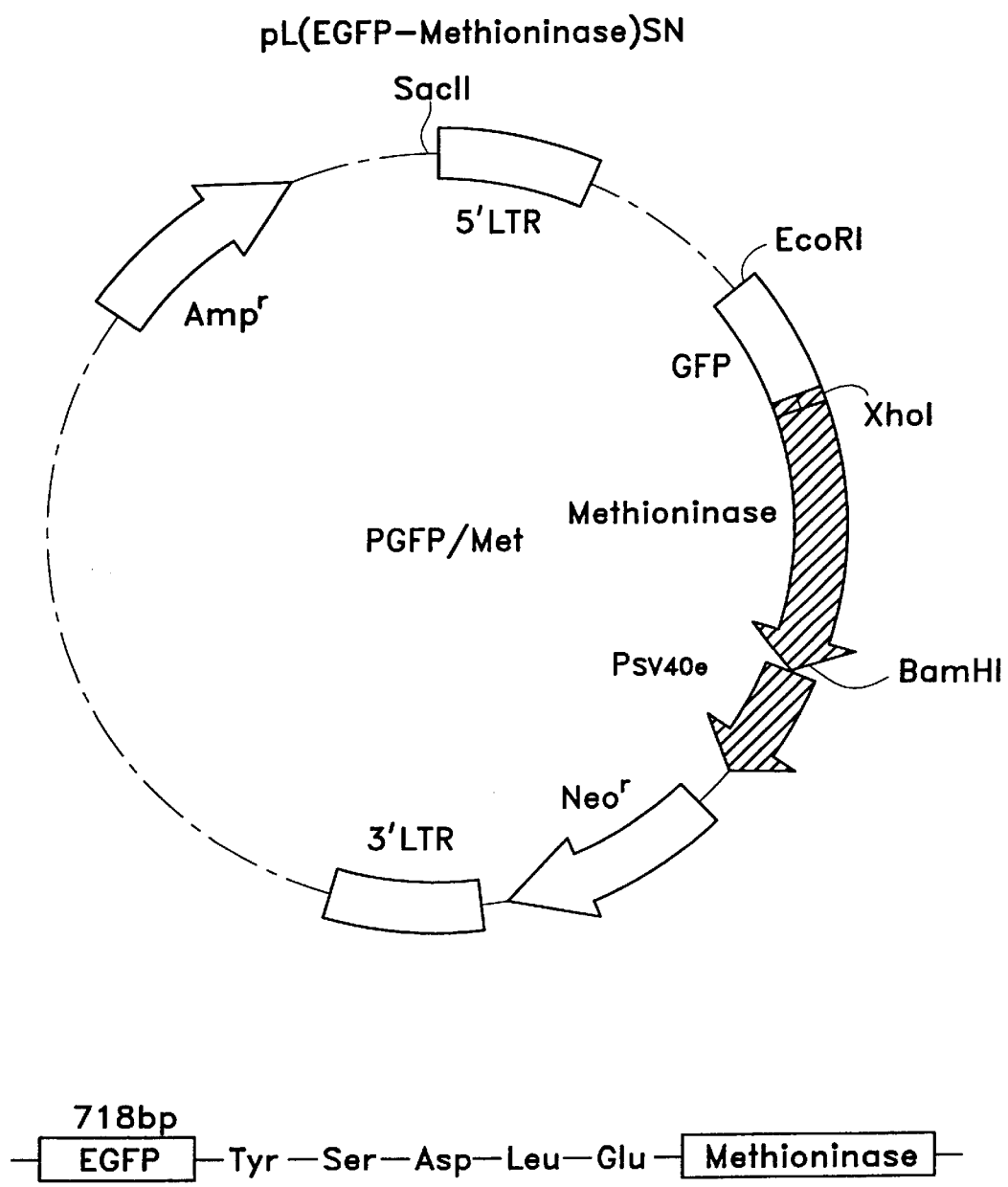
FIGS. 1a and 1b show the construction of expression vectors useful in the invention.

The invention provides model systems for the study of the mechanism of metastasis of tumors generally, as well as to study angiogenesis in solid tumors. Advantage is taken of the visible marker green fluorescent protein (GFP) to label the tumor cells so that their migration and colonization in tissues distal to the tumor can be followed as the migration and colonization progresses. Further, by administering to the subject a contrast dye, such as rhodamine, the growth of blood vessels in solid tumors which have been labeled with GFP can also be observed.

Since sufficient intensity can be achieved to observe the migration of fluorescent cells in the intact animal, in addition to determining the migration of the cells by excising organs, the progression of metastasis can be observed in the intact subject. Either or both methods may be employed to observe metastasis in evaluating, in model systems, the efficacy of potential antimetastatic drugs. The success or failure of treatments provided to patients with potentially metastatic cancers can also be followed using the materials and methods of the invention.

The label used in the various aspects of the invention is green fluorescent protein (GFP). The native gene encoding this protein has been cloned from the bioluminescent jellyfish *Aequorea victoria* (Morin, J. et al., *J Cell Physiol* (1972) 77:313–318). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce. (Prasher, D.C. et al., *Gene* (1992) 111:229–233; Yang, F. et al., *Nature Biotechnol* (1996) 14:1252–1256; Cody, C. W. et al., *Biochemistry* (1993) 32:1212–1218.) Mutants of the GFP gene have been found useful to enhance expression and to modify excitation and fluorescence. GFP-S65T (wherein serine at 65 is replaced with threonine) is particularly useful in the invention method and has a single excitation peak at 490 nm. (Heim, R. et al., *Nature* (1995) 373:663–664); U.S. Pat. No. 5,625,048. Other mutants have also been disclosed by Delagrade, S. et al., *Biotechnology* (1995) 13:151–154; Cormack, B. et al., *Gene* (1996) 173:33–38 and Cramer, A. et al. *Nature Biotechnol* (1996) 14:315–319. Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance. Various forms of GFP exhibit colors other than green and these, too, are included within the definition of "GFP" and are useful in the methods and materials of the invention. In addition, it is noted that green fluorescent proteins falling within the definition of "GFP" herein have been isolated from other organisms, such as the sea pansy, *Renilla reriformis*. Any suitable and convenient form of the GFP gene can be used to modify the tumor cells useful in the models of the invention, and for retroviral transformation of endogenous tumors. The particular humanized hGFP-S65T clone is used in the examples set forth below for illustration.

Techniques for labeling cells in general using GFP are disclosed in U.S. Pat. No. 5,491,084 (supra).

In one application, the method of the invention provides a model system for studying the effects of various therapeutic candidate protocols and substances on metastatic growth of tumors.

In general, the model involves modifying a vertebrate, preferably a mammal, so as to contain tumor tissue, wherein the tumor cells have, themselves, been modified to contain an expression system for GFP. The tumor cells may arise from cell lines of the invention wherein tumor cells have been modified to contain expression systems for GFP and SV40 T-antigen. Tumors can be formed in such vertebrate systems by administering the transformed cells containing the GFP expression system and permitting these transformed cells to form tumors. Typically such administration is subcutaneous and the tumors are formed as solid masses. The tumors thus formed can be implanted in any suitable host tissue and allowed to progress, metastasize and develop.

Suitable procedures for growing the initial tumor, thus, involve transcutaneous injection of the tumor cells producing GFP, such as CHO cells, HeLa cells, carcinoma and sarcoma cell lines, well established cell lines such as the human lung adenocarcinoma line Anip 973, or lung cancer cell line H460 as well as GFP-containing human breast cancer lines MDA-MB468 and MDA-MB435; human prostate cancer lines PC3 and DU-145, human glioblastoma line 324, mouse melanoma B16 and others that may become available in the art, including the immortalized cells of the invention. The administered cells will have been modified to contain an expression system for GFP. After administration, solid tumors generally develop, typically at the site of subcutaneous injection. These tumors, which are themselves fluorescent, can then be removed and used for implantation in the model vertebrate.

Techniques for implantation of the solid tumors, now labeled with GFP, into vertebrates include direct implantation by surgical orthotopic implantation (SOI) at the desired site, typically the site from which the tumor cells were derived. Suitable sites include lung, liver, pancreas, stomach, breast, ovary, prostate, bone marrow, brain, and other tissues susceptible to malignancy. Once the solid tumors have been implanted, the vertebrate becomes a model system for studying metastasis. The tumor is thus allowed to progress and develop and the vertebrate is monitored for appearance of the GFP labeled cells at sites distal from the original implantation site. The monitoring can occur either on the whole vertebrate by opening the animal and observing the organs directly with a fluorescent microscope, or the tissues may be excised and examined microscopically. In some cases the tumors are sufficiently bright that opening the animal is unnecessary—they can be seen directly through the skin. In any case, as GFP is visible to the naked eye, no development systems to stain the tissue samples are required. Tissue samples are simply properly processed as fresh samples in slices of suitable size, typically 1 mm thick, and placed under a microscope for examination. Even colonies of less than 10 cells are thus visible. A variety of microscopic visualization techniques is known in the art and any appropriate method can be used.

It is particularly convenient to visualize the migration of tumor cells in the intact animal through fluorescent optical tumor imaging (FOTI). This permits real-time observation and monitoring of progression of metastasis on a continuous basis, in particular, in model systems, in evaluation of potential anti-metastatic drugs. Thus, the relative lack of metastasis observed directly in test animals administered a candidate drug in comparison to controls which have not been administered the drugs indicates the efficacy of the candidate and its potential as a treatment. In subjects being treated for cancer, the availability of FOTI permits those devising treatment protocols to be informed on a continuous basis of the advisability of modifying or not modifying the protocol.

In addition, the development of the tumor can be studied in vitro in histological culture. Suitable systems for such study include solid supported cultures such as those maintained on collagen gels and the like.

Suitable vertebrate subjects for use as models are preferably mammalian subjects, most preferably convenient laboratory animals such as rabbits, rats, mice, and the like. For closer analogy to human subjects, primates could also be used. Particularly useful are subjects that are particularly susceptible to tumor development, such as subjects with impaired immune systems, typically nude mice or SCID mice. Any appropriate vertebrate subject can be used, the choice being dictated mainly by convenience and similarity to the system of ultimate interest.

Any suitable expression system operable in the tumor cells to be implanted may be used. A number of vectors are commercially available that will effect expression in tumor cells of various types. The nature of the vector may vary with the nature of the tumor and the vertebrate in which it finds its origin. However, when GFP is used to visualize metastasis in a model system, it is preferred to utilize vectors which do not use retroviral or other viral promoters which may complicate the nature of the model.

In order to provide cell lines that are helpful in establishing tumors for these model systems, it is also advantageous to employ expression vectors which provide the cells with the SV40 T-antigen. The presence of this antigen ensures immortality of the culture. Thus, particularly useful in the invention are vectors which comprise expression systems that result in the production both of GFP and SV40 T-antigen.

In order to transfect and modify the transformed cells which are effective in generating tumors, any suitable transfection method may be used, such as liposomes, calcium phosphate precipitation, electroporation and use of a gene gun. Lipofection is preferred.

In contrast, when the method of the invention is used to visualize metastasis in tumors that natively occur in a subject such as a human cancer patient, vectors that employ retroviral or other viral promoters are preferred. The use of such vectors permits the insertion of an expression system for GFP into the already existent tumor. In addition, the expression system may contain nucleotide sequence encoding other useful proteins such as therapeutic proteins which permit simultaneous diagnosis of metastasis and treatment. Among such suitable proteins are included methioninase (see, for example, PCT/US93/11311 and PCT/US96/09935). Such proteins may be produced either as fusions with the GFP, or independently either using a dicistronic expression system or independent expression systems, one for the therapeutic protein and the other for the GFP.

Retroviral based expression systems for GFP have already been described by Grignani, F. et al. *Cancer Res* (1998) 58:14–19 and by Cheng, L. et al. *Gene Therapy* (1997) 4:1013–1022. In these reports, the retroviral expression system itself was used to transfect hematopoietic progenitor cells or packaging cells were employed to provide virus-containing supernatants which can be used directly for infection of the mammalian cells. Thus, in the method of the invention, the tumor contained in the vertebrate subject is typically infected with virus which has been modified and packaged to contain the expression system for GFP. In situ infection with virus results in the ability of the tumor to produce GFP and, in effect, label itself.

Various retroviral systems useful in producing proteins in mammalian cells are known in the art. Examples include commercially available vector and packaging systems such as those sold by Clontech, San Diego, Calif., including their Retro-X vectors pLNCX and pLXSN which permit expression of GFP under a variety of promoters by insertion into the multiple cloning site. These vectors contain ψ* (the extended viral packaging signal) and antibiotic resistance genes for selection. A number of these systems have been developed for use in gene therapy, including vectors which provide a multiple cloning site sandwiched between 5' and 3' LTR derived from retroviral sources, and thus would be useful in labeling the tumors of human patients.

Figure 1B:
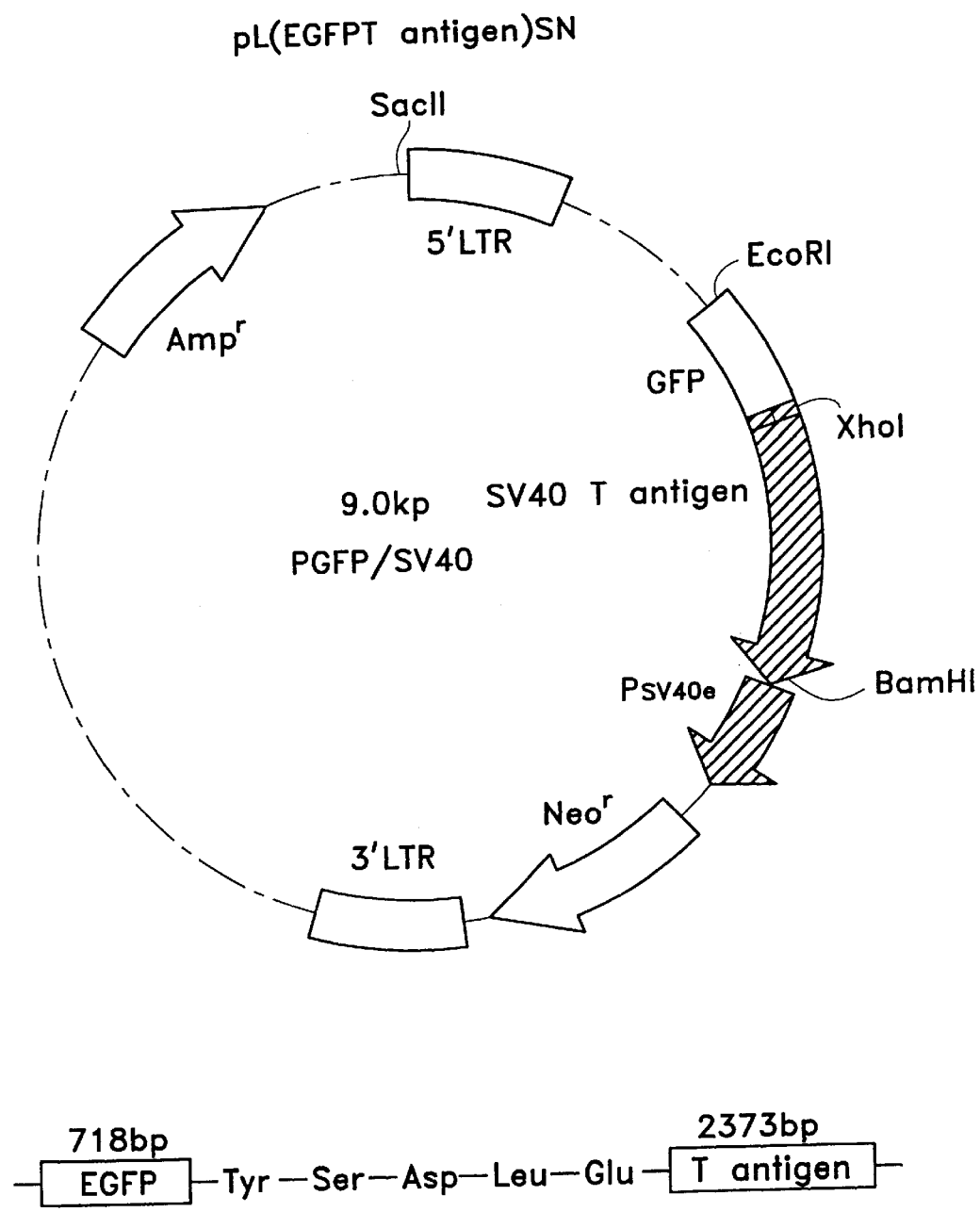

Thus, retroviral based vectors such as those set forth in FIGS. 1a–1b can be transfected into packaging cells and transferred directly to targeted cancer cells or supernatants from the packaging cells can be used to infect tumor cells with the retrovirus. Preferred combinations of retrovirus and packaging cells include the GFP-retrovirus vector pLEIN in PT-67 packaging cells. Co-culture of the packaging cells with colon cancer cells results in transfer of the GFP-retrovirus to the cancer cells.

Using histoculture techniques, and supernatants from PT-67 packaging cells generating GFP-pLEIN virus, the successful modification of a human cancer tissue to display the fluorescence associated with GFP has been demonstrated. For use in vivo, the virus is administered, preferably locally to the tumor, which can be observed within hours after injection either of packaging cells or of the viral containing supernatants. The malignant cells can be identified by their green color, sometimes sufficiently bright so that the tumors can be seen through the skin.

In addition to direct observation of tumor metastasis and growth either in a model system or in a vertebrate, typically mammalian and more typically a human subject which is already afflicted by a tumor, the methods of the invention can be adapted to observe angiogenesis in solid tumors. The tumor is itself labeled with GFP as described above. The subject is then administered a contrast dye, typically by injection, preferably intravenous injection, which allows blood vessels in the tumor to be observed. Suitable dyes include rodamine and other contrast dyes. Any dye which forms a contrasting color with the green color of the GFP can be used. Preferably, the dye is coupled to an inert polymer such as polyethylene glycol to increase the length of time the dye will remain in the blood vessel. A sufficient amount of dye is provided to permit ready visualization; the amount of dye required will depend on the choice of dye, the location of the tumor, the nature of the background GFP, and the method used for observation. Within a few minutes, vessels growing into the solid tumors in such areas as the mesentery, colon wall, and omentum can be observed. Observations can be continued over substantial periods; for example, angiogenesis after several hours is still observed by using this method.

The following examples are intended to illustrate but not to limit the invention.

EXAMPLE 1

Preparation of Tumor Cells that Produce GFP

The humanized hGFP-S65T clone described by Zolotukhin, S. et al., *J Virol* (1996) 70:4646–4654 was used as the green fluorescent protein coding sequence. This codon-optimized gene was purchased from Clontech Laboratories, Inc. (Palo Alto, Calif.) and ligated into the dicistronic expression vector (pED-mtx$^1$) obtained from Genetics Institute, Cambridge, Mass. and described in Kaufman, R. J. et al., *Nucleic Acids Res* (1991) 19:4485–4490. hGFP-S65T was digested with HindIII and blunted; the entire hGFP coding region was excised with XbaI and then unidirectionally subcloned into pED-mtx$^1$ which had been digested with PstI, blunted and then further digested with XbaI.

CHO-K1 cells were cultured in DMEM containing 10% fetal calf serum, 2 mM L-glutamine and 100 $\mu$M nonessential amino acids. Near confluent cells were incubated with a precipitated mixture of LipofectAMINE™ reagent (GIBCO) and saturating amounts of plasmids for six hours and then replenished with fresh medium. The cells were harvested by trypsin/EDTA 48 hours later and subcultured at 1:15 into selective medium containing 1.5 $\mu$M methotrexate (MTX). Cells with stably integrated plasmids were selected in MTX-containing medium and isolated with cloning cylinders (Bel-Art Products, Pequannock, N.J.) by EDTA. After amplification and transfer, Clone-38 was selected because of its high-intensity GFP fluorescence and stability.

In a similar manner, Anip 973 cells, a human lung cancer cell line obtained from Harbin Medical University, China, were cultured as described above for CHO-K1 cells except using RPMI1640 (GIBCO) in place of DMEM. Transfection, selection and amplification and transfer were conducted as described above. Clone-26 was chosen because of its high-intensity GFP fluorescence and stability.

EXAMPLE 2

Mouse Model Using Modified CHO Cells

Clone-38, which was stable at 1.5 $\mu$M MTX and which proliferated at the same rate as the parental CHO-K1 cells as ascertained by comparing doubling times, was used in this model.

Three six-week old Balb/C nu/nu female mice were injected subcutaneously with a single dose of $10^7$ Clone-38 cells that had been harvested by trypsinization and washed three times with cold serum-containing medium and then kept on ice. The cells were injected in a total volume of 0.4 ml within 40 minutes of harvesting and the nude mice sacrificed three weeks after injection. All of the mice had a subcutaneous tumor ranging in diameter from 13.0 mm to 18.5 mm (mean=15.2 mm±2.9 mm). The tumor tissue was strongly fluorescent. It was shown by extracting GFP from cultured Clone-38 cells in comparison to Clone-38 cells prepared from the tumor that the levels of production of GFP were the same in both.

To construct the model, tumor fragments (1 mm$^3$) derived from the nude mouse subcutaneous Clone-38 tumor grown as described above, were implanted by surgical or surgical orthotopic implantation (SOI) on the ovarian serosa in six nude mice as described by Fu, X. et al., *Anticancer Res* (1993) 13:283–286, incorporated herein by reference. Briefly, the mice were anesthetized by isofluran inhalation and an incision was made through the left lower abdominal pararectal line and peritoneum to expose the left ovary and part of the serosal membrane, which was scraped with a forceps. Four 1 mm$^3$ tumor pieces were fixed on the scraped site with an 8–0 nylon suture and the ovary then returned to the peritoneal cavity. The abdominal wall and skin were closed with 6–0 silk sutures.

Four weeks later, the mice were sacrificed and lung and various other organs were removed. The fresh samples were sliced at approximately 1 mm thickness and observed directly under fluorescent and confocal microscopy. Samples were also processed for histological examination for fluorescence and conventional staining. Frozen sections were prepared wherein the slides were rinsed with phosphate buffer saline and fixed for 10 minutes at 4° C.; 10% formaldehyde plus 0.2% glutaraldehyde and PBS were added and the slides were then washed with PBS. The fixed tissue was stained with hematoxylin and eosin using standard techniques.

Light and fluorescence microscopy were carried out using a Nikon microscope equipped with a Xenon lamp power supply and a GFP filter set (Chromotechnology Corp., Brattleboro, Vt.). Confocal microscopy was with an MRC-600 Confocal Imaging System (Bio-Rad) mounted on a Nikon microscope with an argon laser.

The mice, at sacrifice, had tumors in the ovaries ranging in diameter from 18.7 mm–25.3 mm (mean 21.9±3.1 mm). The fresh organ tissues examined under fluorescence microscopy with no treatment of the tissues showed seeding of the tumor throughout the peritoneal cavity, including the colon (6/6 mice), cecum (5/6), small intestine (4/6), spleen (1/6), and peritoneal wall (6/6). Numerous micrometastases were detected in the lungs of all mice and multiple micrometastases were also detected on the liver (1/6), kidney (1/6), contralateral ovary (3/6), adrenal gland (2/6), para-aortic lymph node (5/6) and pleural membrane (5/6). Single-cell micrometastases could not be detected by the standard histological techniques described above and even the multiple cell colonies were difficult to detect using them. As the colonies developed, the density of tumor cells decreased markedly in the center.

In an additional experiment, $5 \times 10^6$ Clone-38 cells were injected into a nude mouse through the tail vein and the mouse sacrificed after two minutes. Fresh visceral organs were analyzed by fluorescence microscopy and showed the presence of fluorescent cells in peritoneal wall vessels which formed emboli in the capillaries of the lung, liver, kidney, spleen, ovary, adrenal gland, thyroid gland and brain.

Thus, using these techniques, progression of micrometastasis can be observed as seeded cells develop into colonies within the relevant target organs. Further, screening for micrometastases can be done easily and quickly in all systemic organs.

EXAMPLE 3

Murine Model Using Human Lung Cancer Cells

The procedures are generally those set forth in Example 2 except that Clone-26 cells as prepared in Example 1 were used instead of Clone-38 CHO cells.

A. As in Example 2, tumors were grown in six-week-old Balb/C nu/nu male mice injected subcutaneously with a single 0.4 ml dose of $10^7$ Clone-26 cells within 40 minutes of harvesting by trypsinization and washing three times with cold serum-containing medium. The cells were kept on ice prior to injection. The animals were sacrificed when the tumors had reached approximately 1.2 cm diameters. The 1.2 cm tumors formed after about 5 weeks.

B. The tumor pieces, 1 mm$^3$, were implanted by SOI into the left visceral pleura of 8 mice as described by Astoul, P. et al., *Anticancer Research* (1994) 14:85–92; Astoul, P. *J Cell Biochem* (1994) 56:9–15, both incorporated herein by reference. Briefly, the mice were anesthetized by isofluoran inhalation an a small 1 cm transverse incision made on the left lateral chest, via the fourth intercostal space, resulting in total lung collapse. Five tumor pieces were sewn together with a 7–0 nylon surgical suture and fixed by making one knot. The lung was taken up by forceps and the tumor sewn into the lower part of the lung with one suture, after which the lung was returned to the chest cavity and the muscles and skin closed with a single layer of 6–0 silk sutures. The lung was reinflated by withdrawing air from the chest cavity with a 23-gauge needle.

C. Four of the mice were sacrificed at 4 weeks and another 4 at 8 weeks. Pleural tumors for the 4-week group ranged from 244.40 mm$^3$–522.88 mm$^3$; those from the 8 week group from 1279.08 mm$^3$–2714.40 mm$^3$. This represented mean volumes of 371 mm$^3$ and 1799 mm$^3$. Specimens of tissue were sliced at 1 mm thickness and observed directly under fluorescent microscopy using a Nikon microscope equipped with a Xenon lamp power supply and a Leica stereo fluorescence microscope equipped with a mercury lamp power supply and GFP filter sets. All of the animals showed chest wall invasion and local and regional spread of the tumor, but in the 8-week mice, all tumors involved the mediastinum and contralateral pleural cavity as well as metastases on the visceral and parietal pleura. Pulmonary hilum lymph nodes were involved in 3 of 4 mice of the 4-week group and all of the mice in the 8-week group. Cervical node involvement was detected in one of the mice of the 8-week group, but no other metastases were observed. The animals were also observed directly before the tissues were excised. The margin of the invading tumor in normal lung tissue could be detected by GFP fluorescence and a small vessel could be seen developing at the margin of the tumor.

D. In an additional experiment, 8 nude mice were injected in the tail vein with a single dose of $1 \times 10^7$ Clone-26 cells that had been harvested by trypsinization and washed 3 times with cold serum-containing medium. The injection contained a total volume of 0.8 ml within 40 min. of harvesting. Again, 4 mice were sacrificed at 4 weeks and another 4 at 8 weeks and tissue specimens were obtained and studied by microscopy as described above. Numerous micrometastatic colonies were detected in whole lung tissue in both groups ranging from 5.2 µm to 32.5 µm in the 4-week group and 5.5 µm–178.3 µm in the 8-week group. The colonies from the 8-week group did not appear further developed as compared with those from the 4-week group. Numerous small colonies ranging in number to less than 10 cells were detected at the lung surface in both groups and brain metastases were detected in 1 mouse of the 4-week group and 2 from the 8-week group. One mouse in the 8-week group had systemic metastases in the brain, the submandibular gland, the whole lung, the pancreas, the bilateral adrenal glands, the peritoneum and the pulmonary hilum lymph nodes.

E. In an additional experiment, similar to that set forth in the previous paragraph, the mice injected in a tail vein with $10^7$ Clone-26 cells were sacrificed at 4, 8 and 12 weeks and the tissues examined as described. Most of the colonies and mice sacrificed at 8 weeks were not obviously further developed compared with those sacrificed at 4 weeks, but numerous small quantities ranging in number down to less than 10 cells and ranging in size from 5.5 µm–110 µm were detected at the lung surface. At 12 weeks, there were many small metastatic colonies which appeared dormant, although other colonies grew extensively by this time, reaching a size up to 1100 µM, suggesting a heterogeneity of dormant and active tumor colonies in the lung.

EXAMPLE 4

Growth of Clone-26 Tumor Cells in Histoculture

Six-week old SCID/SCID mice were injected intravenously with a single dose of $7.5 \times 10^7$ Clone-26 cells which had been harvested by trypsinization and washed 3 times with cold serum-containing medium and kept on ice as described above. The cells were injected in a total volume of 0.5 ml within 40 minutes of harvesting. After 3 weeks, numerous micrometastatic colonies were detected in whole lung tissue up to approximately 550 µm. After 5 weeks, the mice were sacrificed and the Clone-26 seeded mouse lungs were removed and histocultured on spun gels using the histoculture methods developed by Leighton, J. *Cancer Res* (1957) 17:929–941; Leighton, J. et al., *Cancer Res* (1960) 20:575–597; Hoffman, R. M. *Cancer Cells* (1991) 3:86–92. Tumor colonies spread rapidly in the lung tissue over time and after 1 week the tumor cells started to invade and colonize supporting collagen sponge-gel. After 2 weeks, tumor cells formed satellite colonies in the sponge-gel distant from the primary colonies in the lung tissue, thus growing faster in histoculture than in SCID mice. Tumor colonies could grow in histoculture for more than 1 month.

EXAMPLE 5

Construction of a Retroviral Expression Vector for GFP and Preparation of Labeled Tumor Cell Lines FIGS. 1a and 1b show the construction of expression vectors for GFP under control of the SV40 promoter. The constructs employ commercially available pEGFP series vectors available from Clontech. Both bacterial and mammalian expression vectors are available which permit production of additional proteins, as well as GFP, either as fusions or in dicistronic systems. FIG. 1a shows the construction of an expression vector, pGFP/Met, for a fusion of GFP with methioninase; FIG. 1b shows the construction of a vector pGFP/SV40 for production of a fusion protein of GFP with the SV40 T-antigen.

Commercial vectors containing the GFP coding sequence of the desired spectral characteristics using the pLEIN system described in Example 6 were transfected into cell lines originating from tumors, such as human breast cancer, human prostate cancer, human glioblastoma and mouse melanoma. In this manner, human breast cancer cell lines MF-7, MDA-MB468 and MDA-MB435, human prostate cancer cell lines PC3 and DU145, human glioblastoma cell line 324, human lung cancer cells Anip-73 and H460, human colon cancer cells lines Colo-205, HCT-15 and WiDr, human gastric cancer cell line NVGC-4, human kidney cancer cell line SN12C, human tongue cancer cell line SCC-25, human melanomas LOX and SK-mel-5, labeled Chinese hamster ovary cells from cell line CHO-K1 and mouse melanoma cell line B16 labeled with green fluorescent protein were established.

The SV40 T-antigen protein is useful to immortalize cultured cells so as to establish permanent cell lines. Accordingly, the vector pGFP/SV40 is transfected into a series of tumor cell cultures to provide fluorescent immortalized cell lines.

EXAMPLE 6

In Vivo Labeling of Established Tumors

Unlabeled tumors derived from the human lung cancer cell line Anip973 were established in mice using the procedure set forth in Example 3, paragraphs A and B, but substituting unlabeled Anip973 cells for clone 26. The mice were then injected with $1\times10^7$ packaging cells containing the retroviral vector GFP-retrovirus pLEIN contained in PT67 cells. This virus packaging system is available from Clontech, San Diego, Calif. pLEIN contains an insert of the coding sequence for EGFP, a red-shifted variant of wild-type GFP that has been optimized for brighter fluorescence and higher expression in mammalian cells. It has an excitation maximum of 488 nm and an emission maximum at 507 nm. This mutant contains a double amino acid substitution at position 64 from Phe to Leu and at position 65 from Ser to Thr. It is described by Comack, B. et al. *Gene* (1996) 173:31–38. There are more than 190 silent base changes to maximize human codon usage preferences as described by Haas, J. et al. *Curr Biol* (1996) 6:315–324. Thus, pLEIN contains the above-described GFP coding sequence inserted into the multiple cloning site of pLXIN to obtain a dicistronic expression system which permits coordinated translation of the GFP and neomycin resistance. Three days after injection of the cells into the peritoneal cavity of the mice, the tumor cells could be seen in the seminal vesicles under bright-field microscopy and under fluorescent microscopy.

EXAMPLE 7

Observation of Angiogenesis

A suspension containing $1\times10^7$ clone-38 cells, described in Example 1, were injected into the peritoneal cavity of a mouse. Five days later, the mouse was injected in the tail with rhodamine and the mouse was then put under anesthesia and the abdominal cavity opened sufficiently to visualize the tumor. Recovery from this surgery is straightforward. In some cases, abdominal opening is unnecessary as the intraperitoneal tumors can be visualized through intact skin. Tumors were visible in the abdominal cavity and angiogenesis was apparent as identified by the rhodamine fluorescence. Similar results were found in tumors growing in the omentum in the wall of the small intestine, and in the mesentery.

In an analogous experiment, a suspension containing $1\times10^7$ cells of clone-26, described in Example 1, were injected into the peritoneal cavity of a mouse. After one day, tumors appeared in the mesentery and in the colon wall. These were observed by anesthetizing the mouse and a minimal opening of the abdomen. Observations on day 3 of a similarly treated mouse showed tumors in the wall of the small intestine and in the omentum as well as in the colon wall and mesentery. On day 5, a similarly treated mouse was injected in the tail with 100 μl of $2\times10^3$ M rhodamine and a few vessels could be seen in the tumor growing in the mesentery. After day 60, numerous vessels were seen in the tumor growing in the colon wall.

EXAMPLE 8

Construction of Metastatic Models

Using the labeled human cancer cell lines described in Example 5, murine models are established for various types of cancer. The cell lines are implanted into 6-week-old nu/nu female mice with a single dose of $10^7$ GFP expressing human tumor cells which had been harvested by trypsinization and washed three time with cold, serum-containing medium and then kept on ice. The cells are injected in subcutaneous space in the flank of the animal at a total volume of 0.4 ml within 40 min of harvesting. The nude mice are sacrificed to harvest the tumor fragments 3 weeks after tumor cell injection. These tumor fragments are then used for surgical implantation into the corresponding tissue (surgical orthotopic implantation (SOI)) in nude mice as recipients.

The recipient mice are first anesthetized and then implanted using established SOI techniques with fragments of the subcutaneously grown colon cancer, lung cancer, breast cancer, prostate cancer or melanoma. In all cases, except for melanoma, the size of the fragment is 1 mm³; for melanoma, 0.025 mm³ fragments are prepared from the human melanoma LOX-GFP subcutaneous tumor and 5–6 fragments are implanted. The progress of metastasis is then observed using FOTI with a Leica Stereomicroscope MZ12 with a mercury lamp source. GFP is excited with a D425/60 bandpass filter and a 470DCXR dichroic mirror; fluorescence is emitted through a GG475 longpass filter (Chroma Technology, Brattle-boro, Vt.) and collected by a thermoelectrically cooled ST-133 Micromass High-Speed Controlled Camera—TEA/CCD-1317K1 (Princeton Instruments, Trenton, N.J.) with a 17×1035 pixels chip. The images are processed and analyzed with ImagePro+3.1 Software (Media Cybernetics, Silver Spring, Md.). High resolution images are captured by computer, or continuously through video output onto video tape.

In the colon cancer model, a small midline incision is made in the abdomen and the colorectal part of the intestine is exteriorized. The serosa is removed and 8–15 pieces of tumor fragments are implanted. An 8–0 surgical suture is used to penetrate the small tumor pieces and suture them to the wall of the intestine. The intestine is returned to the abdominal cavity and abdominal wall is closed. The animals are then observed for metastases.

For lung cancer models, a small 1 cm transverse incision is made on the left lateral chest via the fourth intercostal space; total lung collapse results. Five tumor pieces sewn together with 8–0 nylon surgical suture are fixed by making one knot; the lung is taken out by forceps and the tumor sewn into the lower part of the lung with one suture. After returning the lung to the chest cavity, the chest muscles and skin are closed. The lung is reinflated by withdrawing air from the chest cavity with a 23-gauge needle. The animals can then be observed for metastasis either by FOTI or by excising various tissues.

For breast cancer, an incision of 1.5 cm is made along the medial side of the nipple and after blunt dissection, the fat pad is exposed. A small incision is made and a small pocket formed to accommodate 2 fragments of the tumor tissue; an 8–0 suture is made to close the pocket. The skin layer is then closed. The animals are then observed by FOTI or by tissue excision.

For prostate cancer, an opening is made above the pubic symphysis to expose the prostate gland. The fascia surrounding the dorsal portion of the prostate and the dorsal lateral lobes of the gland are separated by a small incision. Five randomized fragments are sutured into the incision using a 8–0 nylon suture. The two parts of the separated lobes are sutured together and the surrounding fascia used to wrap this portion of the gland to consolidate the incision. The abdomen is then closed and the animals maintained for observation.

For melanoma, 5–6 fragments are transplanted subdermally into the flank with a 13×¼ cancer implant needle (Popper & Sons, New Hyde Park, N.Y.).

Images can be obtained as described above showing metastases to various locations in the animal.

The animals treated as described above, can then be used to evaluate potential protocols for treatment of cancer and metastasis inhibition. The metastatic progress of the fluorescent tumors in animals administered the protocols is compared to similar animals lacking treatment. The efficacy of the protocols can then be directly observed.

What is claimed is:

1. A method to evaluate a candidate protocol or drug for the inhibition of metastasis of a primary tumor which method comprises:

administering said protocol or drug to a subject which is a mouse, rat or rabbit which contains a primary tumor that stably expresses green fluorescent protein (GFP) in cells of said tumor when said tumor metastasizes and monitoring the progression of metastasis by observing the presence, absence or intensity of the fluorescence at various locations in the treated subject;

wherein said subject contains said tumor that expresses GFP and wherein said subject is a genetically immunocompromised mouse, rat or rabbit, or a mouse, rat or rabbit which is syngeneic to said tumor;

monitoring the progression of metastasis in a control, which contains a similar tumor that expresses green fluorescent protein;

wherein said control subject contains said tumor that expresses GFP wherein said control subject is an immunocompromised mouse, rat or rabbit, or a mouse, rat or rabbit which is syngeneic to said tumor; and comparing the progression of metastasis in said treated subject with the progression of metastasis in said control subject wherein the control subject and treated subject are intact;

whereby a diminution of the progression of metastasis in said treated subject as compared to said control subject identifies the protocol or drug as effective in inhibiting metastasis.

2. The method of claim 1 wherein the progression of metastasis is monitored by fluorescent optical tumor imaging in the intact subject.

3. The method of claim 1 wherein said subject contains said tumor by virtue of surgical orthotopic implantation of said tumor.

4. The method of claim 1 wherein said subject contains said tumor by virtue of injecting cells of a stably transformed tumor cell line which has been transfected with an expression vector containing a first nucleotide sequence encoding green fluorescent protein (GFP) and a second nucleotide sequence encoding a selection marker, both said first and second nucleotide sequences being under control of a viral promoter and wherein said cell line stably effects high level expression of said GFP in the absence of selection agent and maintains a high level expression of GFP when said cell line proliferates through multiple passages of said cell line.

5. A method to monitor metastasis of a primary tumor in a subject which is a mouse, rat or rabbit which contains said primary tumor, and wherein said tumor stably expresses green fluorescent protein (GFP) in cells of said tumor when said tumor metastasizes, wherein said subject contains said tumor that expresses GFP and wherein said subject is a genetically immunocompromised mouse, rat or rabbit, or a mouse, rat or rabbit which is syngeneic to said tumor;

which method comprises monitoring the progression of metastasis by observing the presence, absence or intensity of the fluorescence as a function of time at various locations in said subject wherein the subject is intact.

6. The method of claim 5 wherein the progression of metastasis is monitored by fluorescent optical tumor imaging in the intact subject.

7. The method of claim 5 wherein said subject contains said tumor by virtue of surgical orthotopic implantation of said tumor.

8. The method of claim 5 wherein said subject contains said tumor by virtue of injecting cells of a stably transformed tumor cell line which has been transfected with an expression vector in containing a first nucleotide sequence encoding green fluorescent protein (GFP) and a second nucleotide sequence encoding a selection marker, both said first and second nucleotide sequences being under control of a viral promoter and wherein said cell line stably effects high level expression of said GFP in the absence of selection agent and maintains a high level expression of GFP when said cell line proliferates through multiple passages of said cell line.

9. A method to monitor metastasis of a primary tumor in a mammalian subject which contains said primary tumor, and wherein said tumor stably expresses green fluorescent protein (GFP) in cells of said tumor when said tumor metastasizes, wherein said primary tumor is endogenous to said mammalian subject and expresses said GFP as a result of locally administering a retroviral vector to said subject in the vicinity of said tumor, said retroviral vector containing an expression system for said GFP;

which method comprises monitoring the progression of metastasis by observing the presence, absence or intensity of the fluorescence as a function of time at various locations in said subject.

10. The method of claim 9 wherein the subject is human.

11. The method of claim 9 wherein the progression of metastasis is monitored by excising fresh organ tissues from various locations in said subject.

12. The method of claim 11 wherein said excised tissues are observed by microscopic examination of fresh tissue slices.

* * * * *